United States Patent [19]

Danforth et al.

[11] Patent Number: 5,141,494
[45] Date of Patent: Aug. 25, 1992

[54] VARIABLE WIRE DIAMETER ANGIOPLASTY DILATATION BALLOON CATHETER

[75] Inventors: John W. Danforth, San Francisco; Michael J. Horzewski; Jeff L. Kraus, both of San Jose; Robert D. Lashinski, Cupertino, all of Calif.

[73] Assignee: Danforth Biomedical, Inc., Menlo Park, Calif.

[21] Appl. No.: 481,478

[22] Filed: Feb. 15, 1990

[51] Int. Cl.⁵ .................................................. A61M 29/00
[52] U.S. Cl. ........................................ 604/96; 128/657; 128/772; 604/103; 606/194
[58] Field of Search ................................ 604/96–103; 606/191–194; 128/657, 722

[56] References Cited

U.S. PATENT DOCUMENTS

| | | | |
|---|---|---|---|
| 4,192,305 | 3/1980 | Seberg | 604/165 |
| 4,367,747 | 1/1983 | Witzel | 604/100 |
| 4,641,654 | 2/1987 | Samson et al. | 128/657 |
| 4,655,746 | 4/1987 | Daniels et al. | 604/53 |
| 4,838,269 | 7/1989 | Robinson et al. | 604/194 |
| 4,846,174 | 7/1989 | Willard et al. | 604/95 |
| 4,881,547 | 11/1989 | Danforth | 604/101 |
| 4,884,579 | 12/1989 | Engelson | 128/657 |
| 4,892,519 | 1/1990 | Songer et al. | 606/194 |
| 4,932,959 | 6/1990 | Horzewski et al. | 604/165 |

Primary Examiner—C. Fred Rosenbaum
Assistant Examiner—Chalin Smith
Attorney, Agent, or Firm—Townsend and Townsend

[57] ABSTRACT

A dilatation balloon catheter is disclosed with an inelastic balloon wrapped about a smaller section of a guidewire. During introduction across a region of a stenosis, the balloon is wrapped around a guidewire in such a way that the guidewire contained therein can rotated freely, but cannot advance independently of the balloon. The wrapped configuration is maintained by means of a temporary bond. Inflation of the balloon, following proper positioning of the catheter breaks the bond, permitting the balloon to unwrap from the guidewire contained therein. Typically, the distal end of the guidewire is tapered and the guide wire is controllably clamped to the catheter for advancement into the patient.

13 Claims, 6 Drawing Sheets

FIG._2B. (PRIOR ART)
INFLATED

FIG._2C.
(PRIOR ART)
DEFLATED

VARIABLE WIRE DIAMETER ANGIOPLASTY DILATATION BALLOON CATHETER

BACKGROUND OF THE INVENTION

1. Field of the Invention

This invention relates to catheters and in particular to dilatation balloon catheters, for use in the performance of percutaneous transluminal procedures including peripheral angioplasty, coronary angioplasty and valvuloplasty.

2. Description of the Prior Art

In 1977 Dr. Andreas Greüntzig first used a balloon-tipped flexible catheter to percutaneously dilatate a region of stenosis within a coronary artery of a patient with atherosclerotic heart disease. Since that time, the incidence of percutaneous transluminal coronary angioplasty has increased exponentially. Over the past six to seven years, the performance of this procedure has become routine within many major medical centers throughout the world. With the advent of improved technology and operator skill, the indications for this procedure have also increased substantially.

At the outset of a routine percutaneous transluminal coronary angioplasty procedure, a pre-shaped angioplasty guiding catheter containing a balloon catheter equipped with a flexible intra-coronary guidewire is engaged within the ostium of a coronary vessel containing the lesion to be dilatated. Once suitably engaged (within the left main or right coronary ostium), the guidewire is advanced within the lumen of the appropriate vessel and manipulated across the region of stenosis. By rotating the guidewire, which contains a slight bend within its distal aspect, the operator can control the course of the wire, selecting the appropriate coronary lumen as the wire is advanced.

Once the wire is positioned across the region of stenosis, the angioplasty dilatation balloon catheter is advanced over the guidewire and positioned across the stenotic lesion. The angioplasty is accomplished by inflating the balloon of the dilatation catheter to a high pressure, typically 6 to 10 atmospheres. Generally, 3 to 4 dilatations are required for each region of stenosis. Balloon inflation is maintained for 30 to 90 seconds during each dilatation, depending upon anatomic considerations and operator preference.

Following the final dilatation, the guidewire and balloon catheter are withdrawn leaving the guiding catheter in place. Selective coronary angiography then is performed to evaluate the cosmetic appearance of the vessel following the angioplasty and to determine the severity of the residual stenosis.

Figure 1A:
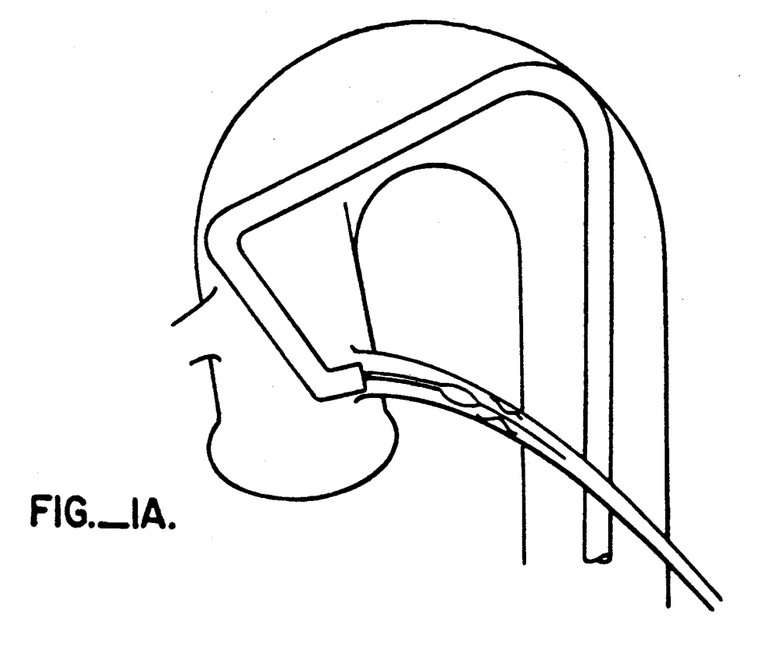
FIG. 1A is a schematic diagram illustrating the normal configuration of a Judkin's guiding catheter within the aorta following engagement within the ostium of the left main coronary artery and introduction of a dilatation balloon catheter over an intra-coronary guidewire to within the proximity of a lesion contained within the left anterior descending coronary artery.
Figure 1B:
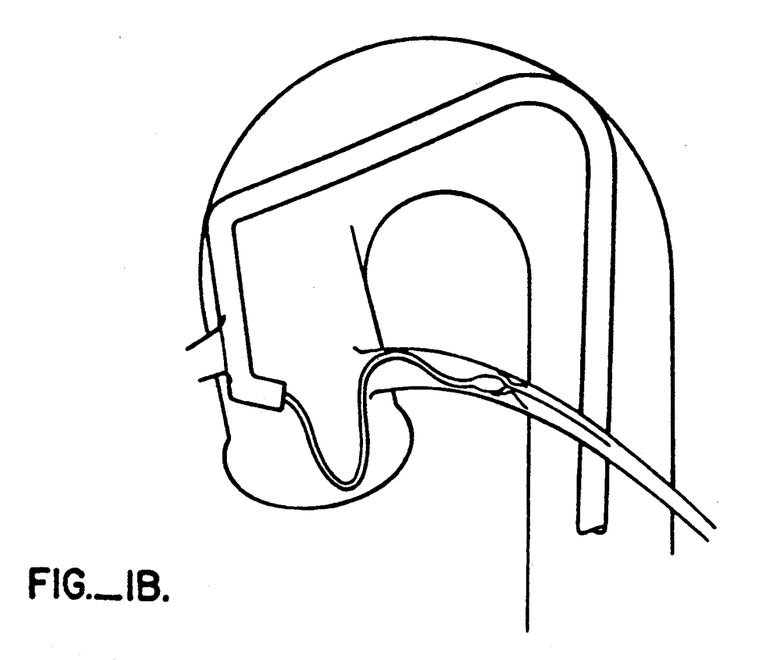
FIG. 1B illustrates the distortion in the configuration of the guiding catheter that frequently results from attempts to advance a dilatation catheter across a stenosis.

At present, the major obstacle to the performance of an angioplasty procedure involves the manipulation of the angioplasty dilatation balloon catheter across the region of stenosis within the coronary artery. The guidewire usually can be advanced across the region of stenosis with relative facility in vessels which are anatomically amenable to the performance of an angioplasty. (See FIG. 1A.) However, manipulation of the balloon catheter across the stenosis often proves difficult because the cross-sectional profile of the distal aspect of the dilatation catheter is considerably greater than the corresponding profile of the intra-coronary guidewire. Advancing the relatively large caliber angioplasty catheter within a significant stenosis commonly results in disengagement of the guiding catheter from the coronary ostium. Once the guiding catheter becomes disengaged, the shaft of the angioplasty catheter frequently prolapses within the sinus of Valsalva immediately cephalad to the aortic valve, precluding further advancement of the distal end of this catheter (see FIG. 1B). The guiding catheter disengages in this circumstance because it is moderately flexible. It must be flexible because insertion of this catheter requires that it be advanced over a guidewire up the aorta, which is relatively straight, and then over the aortic arch, which is, as the name implies, curvilinear.

To circumvent this problem, a variety of "low-profile" catheter systems have been developed including the "semi-movable," "fixed-wire" and "balloon-on-a-wire" systems. The advent of new materials and manufacturing techniques has made possible the miniaturization of "over-the-wire" systems and hence the construction of these devices with lower profiles. These "low profile" systems make possible angioplasty in circumstances previously considered unsuitable for percutaneous transluminal coronary angioplasty.

Although a variety of prior art devices exist for the performance of percutaneous transluminal angioplasty, only "over-the-wire" systems permit the performance of a catheter exchange without the need to sacrifice intra-luminal access.

U.S. Pat. No. 4,323,071 describes a conventional "over-the-wire" angioplasty dilatation balloon catheter. FIG. 2 illustrates the basic configuration of an "over-the-wire" dilatation balloon catheter. A balloon catheter of this functional class consists of a dilatation balloon that is disposed on a dual lumen catheter shaft. The inner lumen of the shaft accommodates a guidewire and functions to provide column support for the dilatation balloon. The outer lumen is continuous with the dilatation balloon and functions to conduct hydraulic pressure along the length of the device. The inner lumen is separate from the outer lumen throughout the length of the catheter.

There are several disadvantages intrinsic to the design and construction of these prior art "over-the-wire" dilatation balloon catheters. For example, the outer surface of the balloon component of prior art "over-the-wire" dilatation balloon catheters invariably contain wrinkles. The wrinkles are caused by the fact that the material used in the construction of these balloons must be relatively inelastic. The wrinkles interface with the endovascular surface of the vessel during introduction of the device within a coronary stenosis and contribute to the friction generated by the catheter during this aspect of the procedure. Additionally, these wrinkles contribute to the cross-sectional profile of the catheter, and hence, contribute to the force necessary to advance the catheter within the confines of a severe stenosis.

These wrinkles further predispose the balloon to the development of perforations. The process of introducing the balloon component of a conventional catheter across intraluminal irregularities (Y-adapter O-ring valves, catheter junctions, and atheromatous lesions) frequently results in the development of shear forces within these wrinkles that cause perforations.

A further difficulty with conventional "over-the-wire" catheters is their non-uniform profile. Typically, the cross-sectional profile of conventional "over-the-wire" dilatation balloon catheters substantially exceeds the corresponding profile of the guidewires contained therein, and the transition from one profile to the other is often abrupt. Hence, the leading edges of conventional "over-the-wire" catheters frequently catch on endovascular obstructions during the course of manipulating these catheters across critical stenoses. This circumstance commonly limits the facility with which these devices can be negotiated within the confines of severe intra-vascular obstructions.

Another disadvantage of conventional "over-the-wire" catheter systems concerns the non-uniform flexibility of such systems. The rigidity of any segment of a conventional "over-the-wire" system is a function of the intrinsic rigidity of the dilatation balloon catheter and the intrinsic rigidity of the wire contained within that segment. Conventional catheters are substantially more rigid relative to the distal components of conventional guidewires. Hence, the introduction of a conventional "over-the-wire" catheter over a guidewire imparts a significant and abrupt increase in the rigidity of the composite system. The abruptness of this change in rigidity limits the navigability of these systems within the confines of complex vascular lesions.

Attempts to miniaturize these conventional "over-the-wire" systems have resulted in several additional functional disadvantages, given the constraints imposed by current technology and material availability. For example, miniaturization has resulted in the manufacture of dilatation catheters with balloons that have lower inflation profiles relative to the previous generation of catheters. Because dilatation balloons must be constructed with materials that are inelastic, there exists a fixed relationship between the inflation and deflation profiles of these balloons. Hence, the construction of low profile conventional dilatation catheters mandates the manufacture of these devices with "low profile" balloons. These "low profile" balloons frequently prove subtherapeutic, thus mandating the use of multiple dilatation catheters of progressively larger size during the course of an angioplasty. The use of multiple catheters in the performance of an angioplasty of a single lesion contributes directly to the expense and complication rate of the procedure and is a limitation intrinsic to the design of conventional "over-the-wire" catheters.

A further disadvantage of miniaturization concerns the sub-optimal torque delivery of the guidewires contained within low profile, "over-the-wire" systems of the prior art. Typically, torque delivery or guidewire "steerability" varies directly with the profile of the mandrel contained within the guidewire. Low profile "over-the-wire" systems contain low profile guidewires that provide limited torque delivery relative to prior generation guidewires of larger profiles.

SUMMARY OF THE INVENTION

The angioplasty dilatation balloon catheter of our invention provides numerous advantages relative to prior art catheters. The configuration of the balloon permits the introduction of a relatively large caliber balloon across a severe stenosis with relative facility. This is achieved by maximizing the ratio of the inflated balloon cross-sectional profile to the corresponding deflated profile. Compared to prior art "over-the-wire" dilatation catheters of commensurate inflated balloon profile, the deflated balloon profile of our device is considerably smaller. As a result, the resistance imparted by the deflated balloon during manipulation of the catheter within a coronary is considerably less than the corresponding resistance imparted by prior art catheters of commensurate inflated profile. Thus, the use of our catheter frequently eliminates the need to install exchange wires, and subsequent larger caliber dilatation catheters, thus precluding the complications associated with these additional procedures. As a result, use of our catheter enhances the efficiency and safety of performing an intraluminal dilatation procedure (e.g., peripheral angioplasty, coronary angioplasty, valvuloplasty, ureteral stenosis dilatation, etc.).

In a preferred embodiment, the catheter includes an inflatable true balloon (i.e., one without an interior tubular structure extending throughout its length) disposed on the distal aspect of the catheter, a channel to accommodate a guidewire extending from the proximal end of the catheter to the proximal end of the balloon, and a separate channel to convey hydraulic pressure that is continuous with the lumen of the balloon. Typically, the balloon is wrapped around the guidewire in a manner such that the exterior surface of the balloon conforms to a channel that accommodates the guidewire contained therein. This wrapped configuration affords several advantages. It provides a compact streamlined means for disposing the balloon in the deflated state while permitting the maximization of the balloon cross-sectional inflation/deflation profile ratio.

In the preferred embodiment, the profile of the deflated balloon approximates the profile of the guidewire distal the balloon. This is achieved by making the guidewire a smaller diameter in the region where the balloon wraps around the guidewire. In one embodiment this configuration is achieved by omitting the coiled layer of wire in the region where the balloon encircles the guidewire.

Figure 2A:
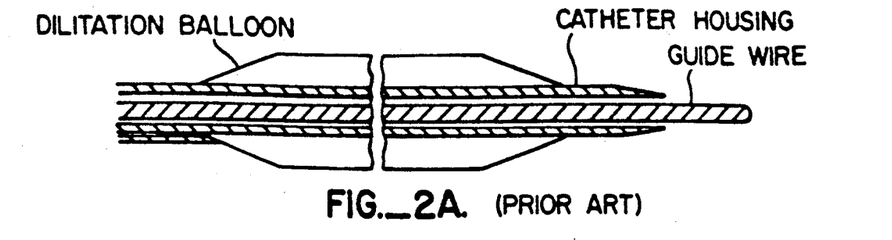
FIG. 2A is a cross-sectional side view of a conventional prior art "over-the-wire" angioplasty dilatation balloon catheter.
Figure 2B:
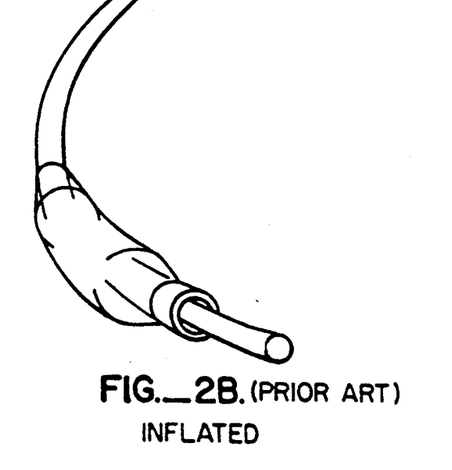
FIG. 2B illustrates the prior art catheter fully inflated.
Figure 2C:
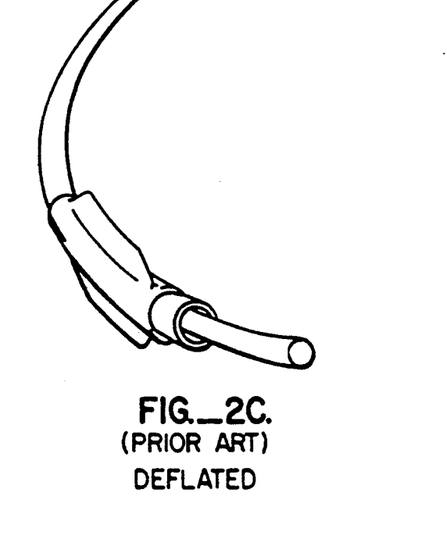
FIG. 2C illustrates the prior art catheter when deflated.
Figure 2D:
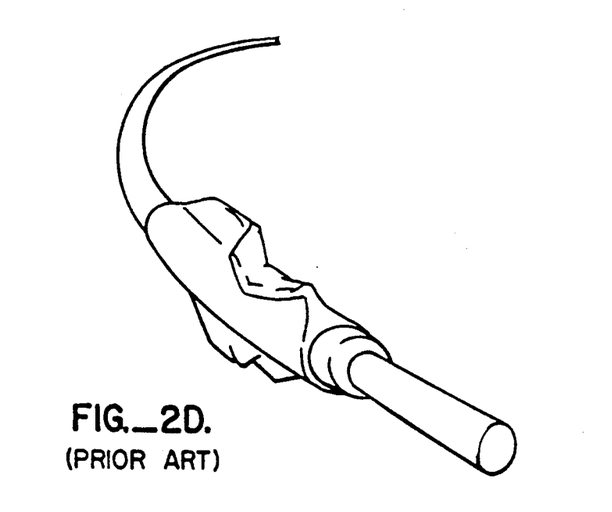
FIG. 2D illustrates the development of wrinkles within the deflated balloon of the prior art consequent with introduction of the dilatation catheter across a region of stenosis.

The use of a true balloon, coaxial wrapping and reversible bonding permits considerable reduction in the deflated cross-sectional balloon profile relative to the corresponding profile of conventional "over-the-wire" catheters because this combination (1) precludes the development of flanges within the balloon (see FIG. 2C); (2) precludes the development of wrinkles at the junction of the balloon and guidewire housing; (3) precludes the development of wrinkles within the surface of the deflated balloon; (4) precludes the need to dispose an inner tubular member within the confines of the balloon; (5) eliminates the bulk intrinsic to the bond between the luminal surface of the balloon and the guidewire housing; and (6) permits the disposal of the balloon component of a separable catheter on a low profile segment of guidewire.

In the preferred embodiment of the catheter, the balloon is reversibly or releasably bonded to itself in the wrapped configuration. This releasable bonding may be achieved by using ultrasonic bonding or various adhesives. The releasable bonding agent or technique enables the dilatation balloon to be maneuvered into position in the region of stenosis while in a wrapped, and therefore smaller cross-sectional profile, and then inflated for treatment of the stenosis. The inflation pressure of the balloon overcomes the reversible bonding and inflates the balloon for treatment of the vessel.

In the preferred embodiment of the catheter, the distal aspect of the guidewire is tapered by tapering the coil of the guidewire. This guidewire configuration provides several functional advantages. It imparts a wedge function to the leading edge of the device that facilitates introduction of the catheter within a region of stenosis. It permits manufacture of the device with a smooth transition zone between the guidewire and balloon component of the system, and it affords some protection for the leading edge of the balloon component of the system. Protection of the balloon is important because the folded configuration of the balloon is prone to the development of mechanically-mediated dehiscence.

In the preferred embodiment, the composite rigidity of the entire system changes gradually from one end to the other. The rigidity of the system derives largely from the rigidity of the mandrel. The mandrel contains a series of tapers throughout its length which function to provide a gradual change in composite rigidity.

In the preferred embodiment, the proximal aspect of the guidewire and catheter components of the system are rotatably and releasably coupled together by means of a pin-vise that is contained within the rotator component of the proximal adaptor. This enables the guidewire to rotate freely within the confines of the catheter, enables the guidewire to contribute to the column strength of the entire system, and permits separation of the guidewire from the catheter.

In the preferred embodiment, a guidewire with a relatively large profile mandrel can be accommodated with minimal impact on the composite profile of the balloon component of the system (the largest profile component of a conventional "over-the-wire" catheter). This makes possible the manufacture of a device with a lower composite balloon profile and superior guidewire "steerability" relative to prior art "over-the-wire" catheters.

In the preferred embodiment, the guidewire contained within this system can be extended to permit the performance of a catheter exchange without the need to sacrifice intra-luminal access. The guidewire contains a proximal adaptor that 'dovetails' with the proximal aspect of an extension wire for this purpose.

In the preferred embodiment, the guidewire contained within this device also can be configured to provide desired column strength to the catheter and thus enhance the "pushability" of the composite system.

In summary, our design permits the manufacture of an ultra-low profile dilatation balloon catheter/-guidewire system with a gradual transition in profile and rigidity between the balloon and guidewire components of the system that: (1) permits the delivery of a relatively inelastic balloon with a lower balloon deflated profile and lower balloon surface coefficient of friction relative to prior art "over-the-wire" systems, (2) permits the complete separation of the catheter component from the guidewire component, (3) permits the performance of a subsequent catheter exchange without the need to sacrifice intra-luminal access, (4) permits infinite guidewire rotational mobility, and (5) provides guidewire enhanced "pushability." In short, our design permits the manufacture of a dilatation balloon catheter that embodies virtually all of the advantages of a conventional "over-the-wire" system and yet circumvents many of the functional limitations intrinsic to the fundamental design of prior art systems of this functional class.

BRIEF DESCRIPTION OF THE DRAWINGS

FIG. 3 illustrates a series of views of the catheter of our design;

FIG. 3B' is a cross-sectional view of the housing of FIG. 3A;

FIGS. 5A-5E illustrate various components of the guidewire contained in this catheter;

DETAILED DESCRIPTION OF THE PREFERRED EMBODIMENTS

Although the configuration of the catheter described herein has application to the performance of a variety of dilatation procedures including peripheral angioplasty, valvuloplasty and dilatation of ureteral stenoses, for the purpose of clarity, the balance of the text will be confined to a discussion of the application of this device to the performance of percutaneous transluminal coronary angioplasty.

Figures 3A, 3B, 3C, 3D, 3E:
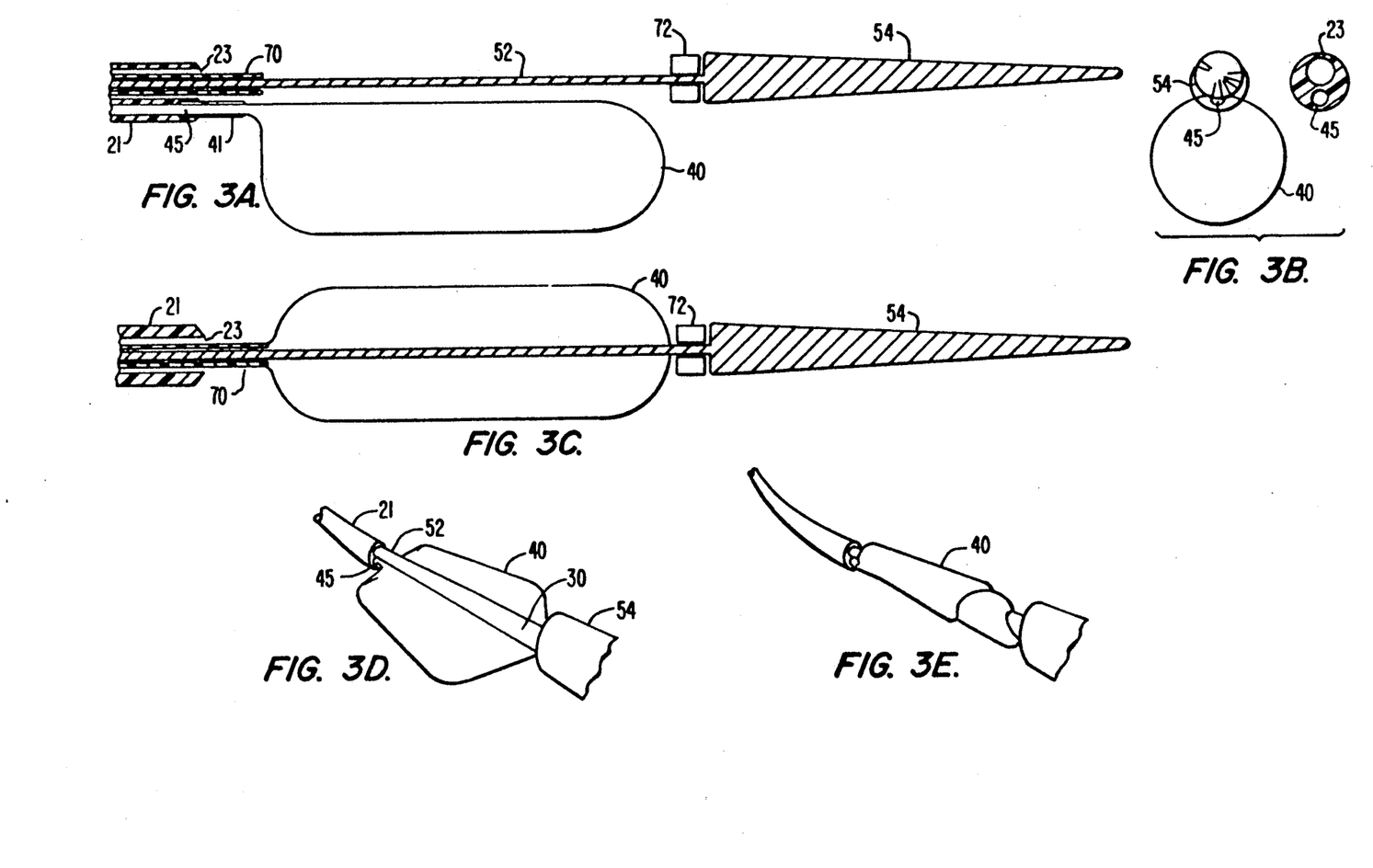
FIGS. 3A, 3B, and 3C are side, end and top views of a preferred embodiment of the catheter.
FIG. 3D illustrates the catheter in perspective view with the dilatation balloon unwrapped.
FIG. 3E is a perspective view of the catheter with the dilatation balloon wrapped around an intra-coronary guidewire.

FIGS. 3A, 3B and 3C are longitudinal, end and top views, respectively, of the angioplasty dilatation balloon catheter of a preferred embodiment of our invention. As shown in FIG. 3, the catheter includes a housing 21 extending from a proximal end (not shown) to a distal end 22 creating a lumen 23 to accommodate an intra-coronary guidewire 50. The shaft contains an additional lumen 45 as shown in FIG. 3B' that communicates with the balloon and functions to convey hydraulic pressure along the length of the device. The balloon typically is formed from an inelastic material so that it will inflate uniformly to a predetermined configuration.

The device further contains a marker chip 41 located immediately proximal to the balloon 40.

FIG. 3B is a "phantom" end view of the catheter illustrating the disposition of channel 45 within the confines of the catheter housing. The communicating channel 45 provides a means for inflating the dilatation balloon 40 once the catheter has been positioned across a region of stenosis. FIG. 3C illustrates the housing 21, guidewire lumen 23, and balloon 40 from above. The balloon is shown in an unwrapped inflated condition.

FIG. 3D is a perspective view of the dilatation balloon 40, in an unwrapped inflated condition. FIG. 3E is a perspective view of the dilatation balloon 40 and guidewire 30 illustrating the manner in which the dilatation balloon may be wrapped around the guidewire. The outside surfaces of the balloon conform to a tube that accommodates the guidewire.

Figures 4A, 4B, 4C, 4D:
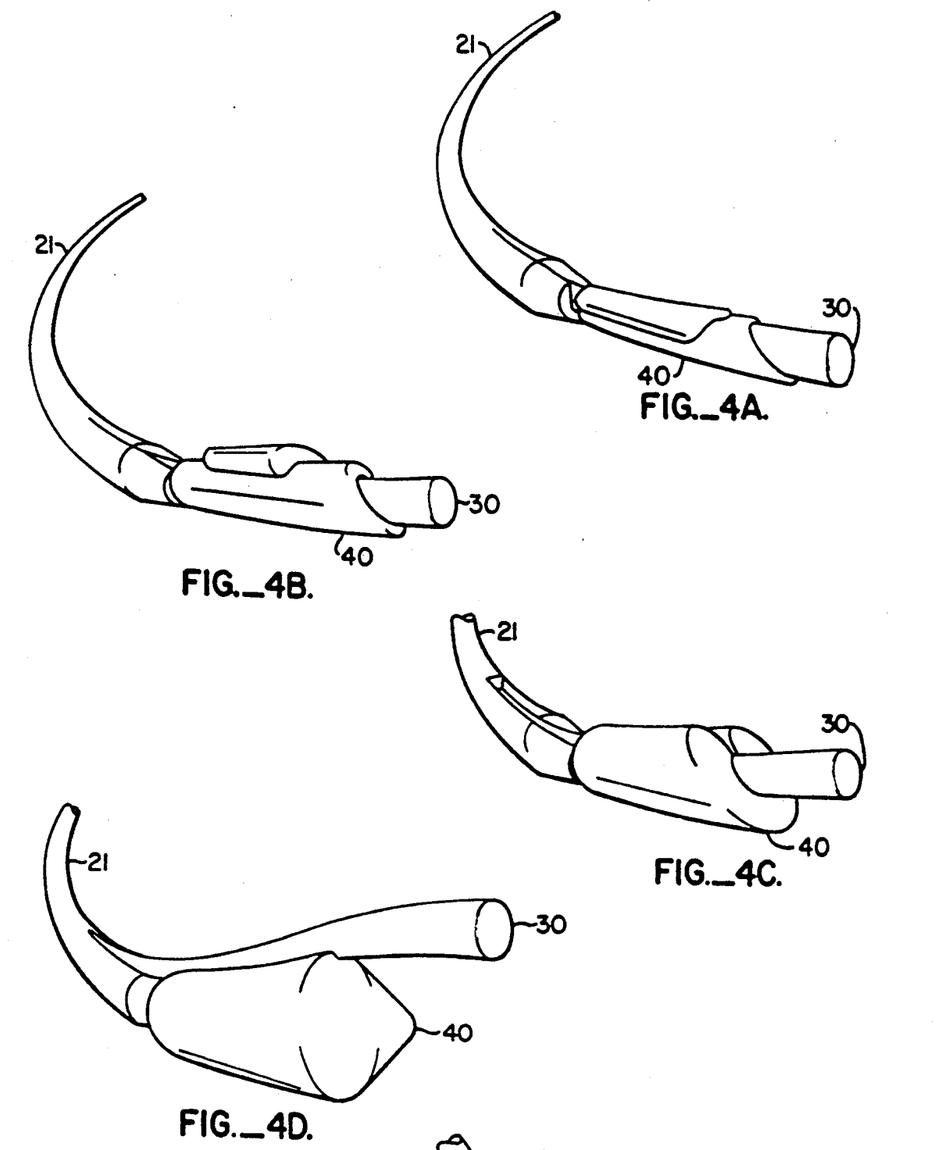
FIGS. 4A-4D are a sequence of views illustrating the inflation of the dilatation balloon.

FIGS. 4A-4D illustrate the manner in which the wrapped balloon unwraps during inflation. When first manipulated across a stenosis, balloon 40 is wrapped in the manner of FIG. 4A. This configuration is maintained by a temporary bond designed to tolerate the stresses usually applied to this segment of the catheter during introduction across a coronary stenosis and yet release when subjected to the forces that develop during inflation of the balloon. This bonding may be achieved using any well known technique including, for example, ultrasonic bonding or adhesives. As shown in FIGS. 4B and 4C, inflation of the balloon requires breaking the bonds that maintain the balloon in the wrapped configuration. As the balloon inflates, it unwraps from the guidewire and no longer encompasses the guidewire. Balloon inflation is accomplished by the infusion of fluid into the balloon via hydraulic channel 45 that is contained within the catheter shaft. Once it is completely unwrapped, as shown in FIG. 4D, the guidewire is no longer encompassed by the balloon, and hence the catheter is free to move in a coaxial direction relative to the guidewire.

Figure 4E:
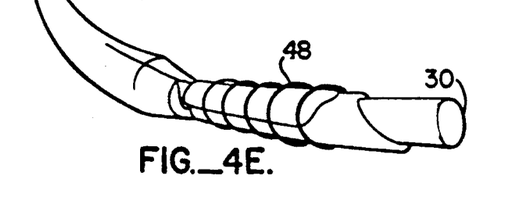
FIG. 4E illustrates a stent on the catheter.

In an alternate embodiment shown in FIG. 4E, a stent 48 is used to maintain the balloon 40 in a wrapped position. When the balloon 40 is inflated, the stent 48 is deformed to an enlarged shape and remains within the artery to hold the lumen open. Thus, the catheter functions as an optimal device to introduce stents into the vasculature.

Figure 5A:
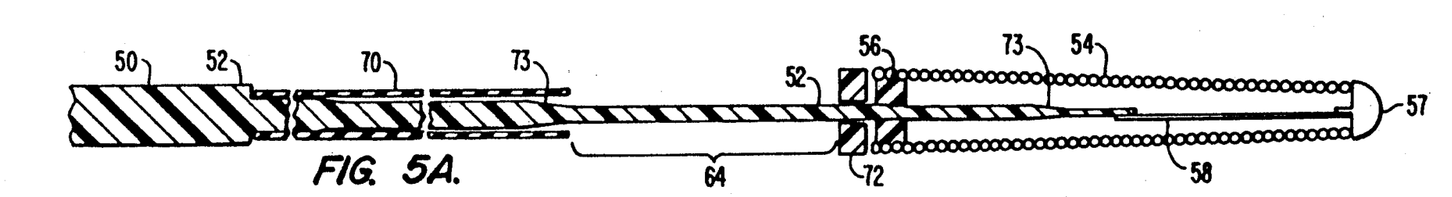
FIG. 5A illustrates a profile phantom view of the distal aspect of the guidewire.
Figure 5B:
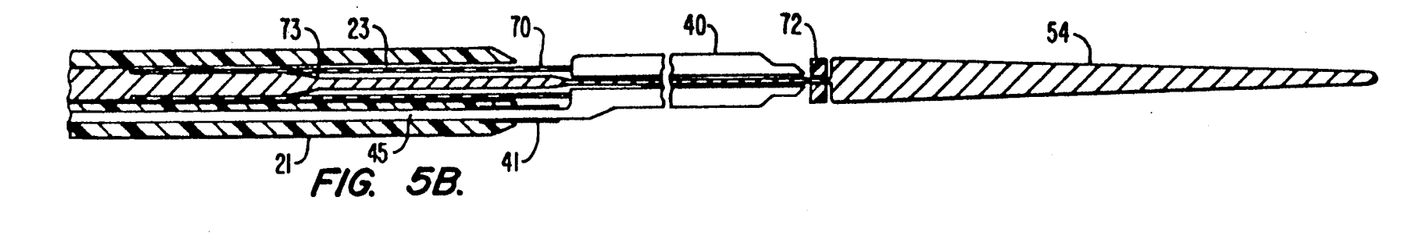
FIG. 5B illustrates a schematic phantom profile view of the distal aspect of the composite catheter and guidewire system of our design.

FIG. 5A is a profile view of a preferred embodiment of the guidewire 50. The wire 50 consists of a progressively tapered mandrel 52 about the distal aspect of which a wire is coiled. The platinum alloy wire coil 54 is secured to the mandrel 52 by means of a joint 56, a wire tip 57 and a wire ribbon 58. Specifically, the distal aspect of the mandrel is flattened and bonded simultaneously to the proximal aspect of the platinum coil and guidewire ribbon 58 by means of a solder joint. The distal aspect of the platinum coil is secured to the ribbon by means of a solder joint. In the case of this latter joint, the solder is configured to impart a rounded tip to the guidewire coil. The ribbon 58 measures approximately 0.001 inches in thickness, by 0.003 inches in width by 1-2 centimeters in length, and it is composed of stainless steel. The balloon is wrapped with a close tolerance gap around the mandrel in region 64. Wrapping the balloon around a low profile segment of the guidewire 64 permits the construction of a guidewire-directed balloon delivery system with a particularly low composite cross-sectional profile in the region of the dilatation balloon, the largest profile component of prior art "over-the-wire" systems. (See FIG. 5B.) This approach further permits the manufacture of a balloon delivery system with an infinitely rotatable guidewire that contains a smooth transition zone between the balloon and guidewire components of the system. (See FIG. 5B.)

Our invention further permits the manufacture of a guidewire-directed balloon delivery system that provides greater "steerability" relative to "over-the-wire" catheter systems of conventional design. The "steerability" of a catheter/guidewire system varies directly with the profile of the guidewire mandrel. As shown, our invention permits the disposal of a balloon over a segment of guidewire lower in profile compared to the majority of the mandrel. Thus, our invention permits the manufacture of a low profile system that contains a larger profile mandrel relative to the mandrel profiles of guidewires that can be accommodated within "over-the-wire" systems of commensurate composite deflated balloon profile. As a result, our design permits the manufacture of a highly steerable system.

Our invention further permits the manufacture of a low profile, highly steerable guidewire directed balloon delivery system with a gradual transition in composite rigidity. In general, the rigidity of the entire system derives largely from the rigidity of the mandrel contained therein. Because the mandrel is tapered, the transition in rigidity occurs gradually along the length of the device. The distal end of the device is more flexible relative to the proximal end and hence more suited for introduction within the frequently tortuous confines of the vasculature. The balloon 40 and tubular member 70 can be constructed such that the rigidity of these components complements the rigidity of the respective segments of the guidewire.

The profile of the guidewire coil 54 is non-uniform. This feature imparts a wedge function to the leading edge of the device and permits the coils to protect the delicate leading edge of the balloon 40 from potential trauma that could develop during the process of manipulating the balloon component of the device within the confines of an intra-vascular lesion. FIG. 5A also illustrates two optional guidewire components 70, 72. The first is a length of tubing 70 that is disposed over mandrel 52. This tubing protects the delicate mandrel from potential trauma during the course of a catheter exchange and confers column strength and therefore "pushability" to the catheter. This is discussed further below. The second optional component is a small gasket 72 disposed on the mandrel 52 at the interface between the leading edge of balloon 40 and the proximal end of coil 54. This gasket protects the delicate thin-walled balloon from any sharp edges within the joint 56 and coil 54.

Figure 5C:
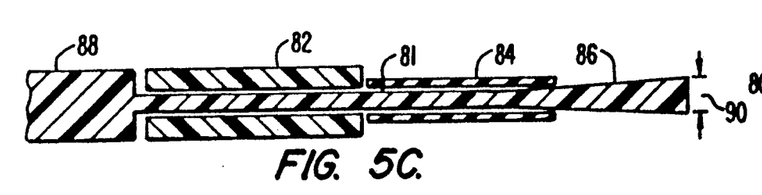
FIG. 5C illustrates the configuration of the distal end of an extension wire that is designed to dovetail with the proximal aspect of the system guidewire.
Figure 5D:
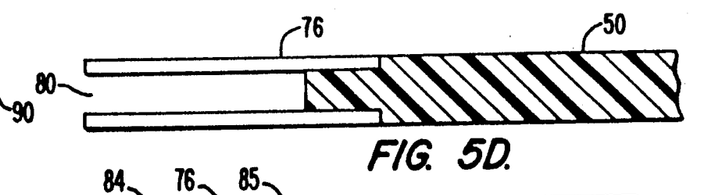
FIG. 5D illustrates a phantom profile view of the proximal aspect of the guidewire and extension mechanism.
Figure 5E:
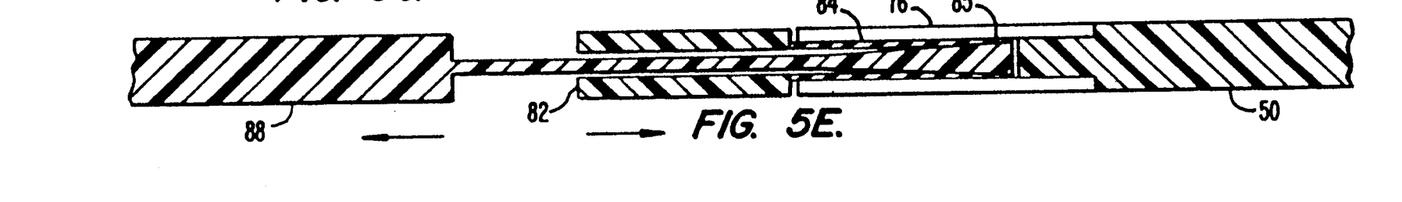
FIG. 5E illustrates the method of seizing the coupling between the guidewire and extension wire.

FIG. 5D is a profile view of the proximal end of the guidewire 50 contained within the dilatation balloon catheter/guidewire system of our design. The proximal end is welded in a coaxial manner to a length of hypotubing 76 that contains a lumen 80. This configuration permits extension of the guidewire by means of a "male-to-female" coaxial joint if a catheter exchange is required. FIG. 5C illustrates the corresponding "male" component of the extension wire 88 which consists of a core element 81 having a reverse taper in region 86, and two tubular members 82, 84 slidably disposed thereon. Tubular member 84 is preferably constructed of a compliant and relatively tacky material such as low density polyethylene. Tubular member 82 is preferably constructed of a relatively rigid and smooth material such as stainless steel. The profile 90 of the distal aspect of the core element 81 approximates the dimensions of lumen 80, and yet the profile 90 of the core element is sufficiently small to permit introduction of the core element 81 into the lumen 80 of guidewire 50 with minimal resistance. FIG. 5E illustrates the means by which the joint between the guidewire 50 and the extension wire 88 is secured. Following insertion of the core element 81 into the lumen 80 of guidewire 50, the operator holds onto the extension wire 88 and the tubular element 82 and pulls these two elements away from one another. This maneuver forces the malleable tubular element 84 into the interface 85 between the luminal surface of the guidewire 50 and the outside surface of the core element 81 and generates a compression seal between these two surfaces that secures the extension wire 88 to the guidewire wire 50.

Figure 6:
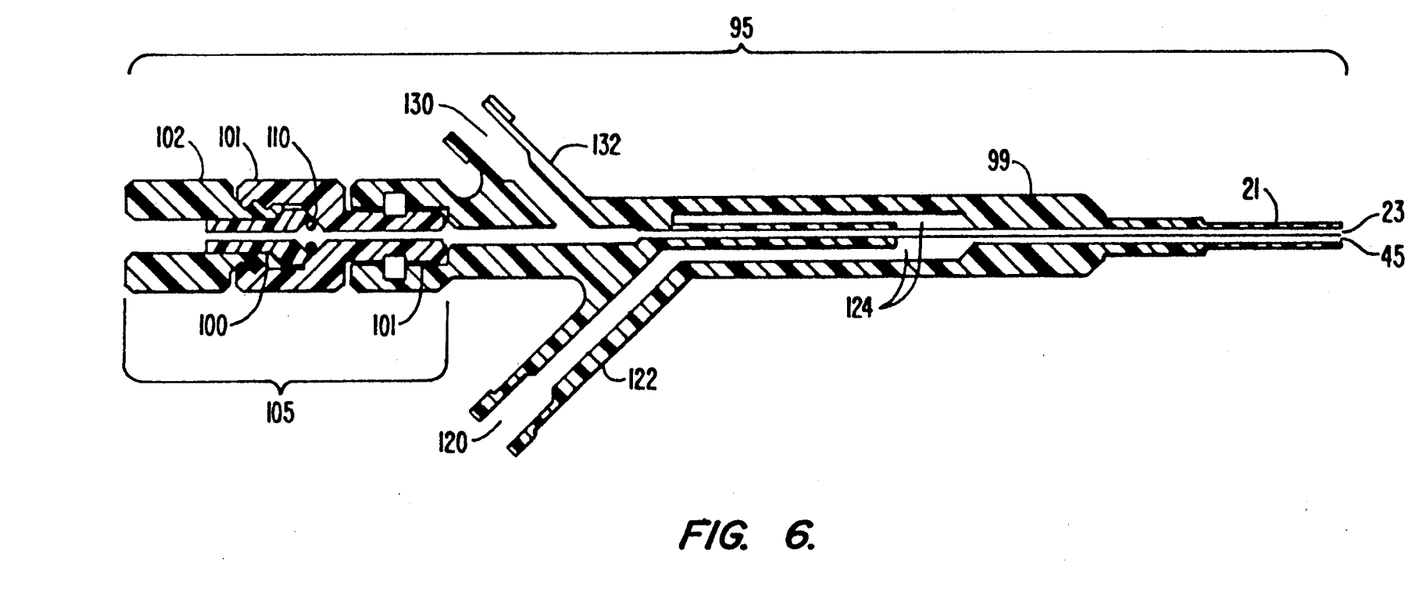
FIG. 6 illustrates a cross-sectional view of the proximal adaptor.

FIG. 6 is a profile view of the proximal adaptor 95 of the invention illustrating a pin-vise 100 that is contained within a permanently attached and rotatably disposed two component rotator 105. The pin-vise releasably couples the catheter to the guidewire 50. The rotator 105 facilitates operator control of guidewire rotation and maintains the coaxial relationship of the guidewire component relative to the catheter component of the system. According to one aspect of the invention, the rotator 105 provides a device for controllably securing the channel 45 to the guidewire 50 to thereby enable advancement and retraction of the channel 45, balloon 40, and guidewire 50 together. According to one embodiment of the invention, the means for controllably securing comprises a clamp 101, 102. According to one embodiment of the invention, the clamp comprises an adjustable O-ring 110. The magnitude of the grip applied on the guidewire by the rotator can be adjusted by rotating one of the rotator components 101 relative to the other 102. Because of a right-hand screw at the interface between the rotator components, clockwise rotation of component 102 relative to component 101 enhances the compression force applied by the pin-vise to the guidewire and hence seizes the rotator to the guidewire. Counterclockwise rotation of 102 relative to 101 accomplishes the opposite effect and releases the rotator from the guidewire.

The catheter system of our invention offers several advantages over conventional low profile, "semi-movable", "fixed-wire" and "balloon-on-a-wire" catheter systems because it permits the expeditious delivery of a large profile balloon with a low composite deflated profile over an infinitely rotatable high torque guidewire. Furthermore, the use of this device does not mandate the sacrifice of intra-luminal access in the event of a catheter exchange.

The catheter system of our invention offers several advantages over low profile "over-the-wire" prior art catheter systems as well, because it permits the delivery of a larger profile balloon over a more torqueable and more stable guidewire with a smaller composite deflated profile, smoother balloon/guidewire transition, and lower balloon surface coefficient of friction.

The fundamental limitation inherent to all "over-the-wire" balloon delivery systems concerns the resistance to passage of the balloon component of the system across regions of stenosis. Provided that the vessel is patent, then it is generally feasible to advance the guidewire across an intra-luminal obstruction without difficulty in the large majority of cases. However, manipulation of the balloon component of the system within the confines of a stenosis frequently proves more difficult.

Several factors contribute to this disparity. To begin, the cross-sectional profile of the balloon component of conventional "over-the-wire" catheters is considerably larger than the corresponding profile of the guidewire contained therein, and resistance varies as a function of profile. "Wings" disposed along the external surface of deflated balloons of conventional design contribute to the profile of prior art balloon dilatation catheters. The tubular members disposed inside the "over-the-wire" balloons of conventional design further contribute to the composite profile of these devices. Secondly, the coefficient of friction of prior art deflated balloons commonly exceeds the corresponding property of the teflon TM -coated guidewires installed therethrough. Thirdly, the leading edge of the catheter component of "over-the-wire" systems of the prior art terminates abruptly. Hence, the leading edges of these devices tend to "hang up" on intra-vascular gruel as these catheters are being advanced within the confines of intravascular lesions. Finally, the introduction of prior art "over-the-wire" catheters over guidewires abruptly increases the rigidity of these composite systems, and this circumstance tends to distort the paths of these devices as they are being introduced across lesions, a circumstance that tends to further compromise the navigability of these devices within the confines of complex lesions.

The deflated cross-sectional profile of our catheter is substantially smaller than the corresponding profiles of all currently available "over-the-wire" catheter systems. By reducing the profile of the guidewire contained within the balloon and by eliminating the tubing that constitutes the housing for the guidewire within the confines of prior art "over-the-wire" balloons, a considerable amount of the bulk that contributes to the deflated cross-sectional profile of the catheter system is eliminated. Also eliminated is the need to attach the deflated (and hence planar) balloon to the circumference of the tubing, a geometrical incongruity that frequently leads to the development of wrinkles. The use of a true balloon, reversible wrapping of the balloon around the guidewire to conform the balloon to a tube that accommodates a freely rotatable guidewire, and the use of a guidewire that contains a low profile segment in the region contained by the balloon, provides a means of disposing a potentially separable large profile balloon on a generally large profile guidewire mandrel with a particularly small composite cross-sectional deflated balloon profile. This feature allows an operator to readily introduce a dilatation balloon of optimal inflated caliber across a stenosis at the outset of the procedure. It thereby potentially precludes the need to install and inflate additional dilatation balloon catheters of sequentially larger caliber.

Because the balloons used in the construction of conventional catheters have very thin walls, the wrapping of a relatively large balloon around a guidewire does not lead to a significant increase in the overall deflated cross-sectional diameter of the catheter relative to the corresponding profile of a catheter containing a smaller caliber dilatation balloon. Hence, the advantage of our design from the standpoint of profile is increasingly apparent with progressively larger balloon sizes. In one embodiment, our configuration permits the disposal of an inelastic 3 mm balloon that has a wall thickness of 0.0008 inches over a 0.006 inch segment of the guidewire with a composite profile of 0.035 inches and a guidewire-balloon clearance of 0.003 inches.

In addition to profile considerations, the use of our balloon design and reversible or releasable bonding circumvents the development of wrinkles and wings and permits the construction of a dilatation balloon with a streamlined surface and low coefficient of friction in the deflated state. Balloons of conventional design invariably wrinkle when deflated. Polyethylene terephthlate (PET), a popular material for use in the construction of the balloon component of angioplasty catheters is particularly prone to the development of wrinkles. The presence of these wrinkles, as explained above, contributes dramatically to the coefficient of friction of the surface of the balloon component and increase the likelihood of damage to the balloon during introduction.

Our design permits the manufacture of a low profile guidewire-directed balloon delivery system that permits the performance of a catheter exchange without the need to sacrifice intra-luminal access. The guidewire 50 can be extended to conform to the dimensions of a conventional exchange guidewire, the guidewire can be released from the catheter component of our system by counterclockwise rotating component 102 relative to component 101 and the catheter can be withdrawn over the extended guidewire, following balloon inflation. The performance of these three procedures in sequence leaves a guidewire continuously installed within the confines of the vessel requiring dilatation, following insertion and removal of the catheter component of our device, of suitable length for the performance of a catheter exchange, that will accommodate many of the currently available "over-the-wire" dilatation balloon catheters. Hence, our system permits the performance of a catheter exchange, without sacrificing intra-luminal access.

Currently, only "over-the-wire" catheters permit the performance of a catheter exchange without the need to sacrifice intra-luminal access, and this feature constitutes the principal advantage of prior art "over-the-wire" catheter/guidewire systems relative to prior art "semi-movable", "fixed-wire" and "balloon-on-a-wire" systems. Thus, this advantage of our device circumvents the need to renegotiate the confines of the vessel with a guidewire in the event that the installation of a second catheter is required. It permits the performance of an exchange procedure with greater efficiency relative to "semi-movable", "fixed-wire" and "balloon-on-a-wire" systems that do not offer this advantage. It circumvents the risk of introducing the second catheter within the confines of a balloon-mediated rupture of the intima created by inflation of the first catheter, because the second catheter is compelled to travel along the course of the guidewire. Finally, it provides intra-luminal access for the installation of a bail-out catheter in the event that the vessel occludes in response to balloon-mediated dilatation. In short, this feature permits the performance of a catheter exchange with greater safety and efficiency relative to catheter systems that do not offer this advantage.

Our invention further permits the manufacture of a safe, low profile guidewire-directed balloon delivery system that contains a smooth surface transition between the balloon and guidewire components of the system. This feature is a particular advantage relative to all other catheter systems of the prior art that permit the separation of the catheter from the guidewire component of the system (e.g., "over-the-wire" systems). These prior art catheters all contain a leading edge that terminates abruptly, with the disadvantages discussed above. Our invention minimizes the propensity for our device to "hang up" and thus facilitates the process of introducing our device within the lumen of a complex lesion. The wedge aspect of our system facilitates introduction of the device within a critical stenosis.

Our design further permits the manufacture of a safe, low profile, smooth guidewire-directed balloon delivery system that has a gradual transition in composite rigidity from one end to the other. This feature constitutes a profound advantage relative to all prior art systems that permit separation of the catheter component from the guidewire component of the system (e.g., "over-the-wire" systems). Because catheters are more rigid than the distal aspects of guidewires, the introduction of a prior art catheter over a guidewire creates an abrupt increase in the rigidity of the component "over-the-wire" catheter/guidewire system. This abrupt transition in rigidity tends to distort the path of the catheter and compromises the navigability of the system within the confines of complex lesions. Our design circumvents this inevitability because the coaxial relationship of the balloon and guidewire do not change during the course of introducing the device within the vasculature. As a result, the device can be manufactured with components of complementary intrinsic rigidity. In short, the design affords manufacture of the device with a gradual transition in composite rigidity. The rigidity of the entire system derives largely from the rigidity of the mandrel contained therein. Because the mandrel is tapered, the transition in rigidity occurs gradually along the length of the device. The distal end of the device is more flexible relative to the proximal end and hence more suited for introduction within the frequently tortuous confines of the vasculature. The balloon 40 and tubular member 70 can be constructed such that the rigidity of these components complements the rigidity of the respective segments of the guidewire.

Our design further permits the manufacture of a safe, low profile, smooth guidewire-directed balloon delivery system that provides greater "steerability" relative to very low profile "over-the-wire" catheter systems of conventional design. The "steerability" of a catheter/guidewire system varies directly with the profile of the guidewire mandrel. Our design permits the disposal of a balloon over a segment of guidewire that is lower in profile relative to the majority of the mandrel. Conversely, prior art "over-the-wire" catheters do not. Hence, our design permits the manufacture of a low profile system that contains a larger profile mandrel relative to the mandrel profiles of guidewires that can be accommodated within "over-the-wire" systems of commensurate composite deflated balloon profile. As a result, our design permits the manufacture of a highly steerable system.

Our design further permits the manufacture of a safe, low profile, smooth, and highly steerable guidewire-directed balloon dilatation system that provides infinite guidewire rotational mobility. This feature constitutes a profound advantage of our system relative to prior art "fixed-wire" systems. Conventional "fixed-wire" systems can be manufactured with similar composite cross-sectional balloon profiles. However, these devices do not permit infinite guidewire rotational mobility, and their use requires sacrificing intra-luminal access in the event that a catheter exchange is required.

Our design further permits the manufacture of a safe, low profile, smooth, guidewire-directed, highly steerable balloon delivery system that has guidewire-enhanced "pushability." This feature enhances the potential for the balloon component of our device to be introduced within the confines of complex lesions. "Pushability" is one of the most critical functional characteristics of a balloon dilatation catheter. The "pushability" of a conventional catheter relates to the column strength of the shaft of the catheter, which, in turn, relates primarily to the rigidity of the polymer used in the construction of the catheter shaft and to the thickness of the shaft walls. Because of a need to maintain flexibility within the system, particularly rigid plastics are precluded. Similarly, the need to construct these devices with low shaft profiles precludes the development of these devices with thick shaft walls. For these reasons, prior art "over-the-wire" catheters tend to have limited "pushability." Our design affords a unique opportunity to use the guidewire to enhance the column strength and hence "pushability" of the system. Because metal is less prone to coaxial compression relative to plastic, the guidewire has greater intrinsic "pushability" relative to the catheter shaft. The pin-vise contained within the rotator of the proximal adaptor of our design functions to maintain the coaxial relationship between the guidewire and catheter components of the system. The tubular member 70 functions to maintain the coaxial relationship between the guidewire and the balloon. Thus, the application of coaxial force to the proximal adaptor results in the efficient transmission of force to the guidewire/balloon interface. This configuration enables the operator to drive the balloon component of the system across a lesion by applying force to the proximal adaptor (and hence guidewire). This feature, in turn, minimizes the need to manufacture the catheter component of the system in a manner that resists coaxial compression and thus makes possible the manufacture of the catheter shaft with thin, flexible walls and a low profile. This feature, in turn, permits the manufacture of the device with larger lumens and greater flexibility relative to devices with commensurate "pushability" and shaft profile. Hence, our design further permits the manufacture of a flexible balloon delivery system with a relatively large profile hydraulic channel 45 that affords greater "pushability" relative to prior art "over-the-wire" systems of similar shaft composition and profile.

The foregoing has been a detailed description of the preferred embodiment of the invention. Although specific details have been described to enable a clearer understanding of the invention, the scope of the invention may be ascertained from the appended claims.

We claim:

1. A catheter comprising:
   a guidewire extending from a proximal end to a distal end, the guidewire including a first portion along its length near the distal end having a reduced cross-section than in portions elsewhere;
   an inflatable dilatation balloon coupled to the guidewire by being wrapped around the guidewire in the first portion; and
   means communicating with the balloon for inflating it.

2. A catheter as in claim 1 wherein the balloon is releasably coupled to the guidewire.

3. A catheter as in claim 2 wherein the balloon is releasably coupled to the guidewire by being temporarily attached to itself where it is wrapped around the guidewire.

4. A catheter as in claim 1 wherein the balloon is unwrapped from the guidewire when it is inflated.

5. A catheter comprising:
   a guidewire extending from a proximal end to a distal end, the guidewire including a first portion along its length near the distal end having a reduced cross-section than in portions elsewhere;
   an inflatable dilatation balloon coupled to the guidewire in the first portion; and
   means communicating with the balloon for inflating it wherein the guidewire comprises:
   a core region extending from the proximal end to the distal end; and
   a surrounding region of material encompassing the core region except in the first portion.

6. A catheter as in claim 5 wherein:
   the core region is tapered at its distal end.

7. A catheter as in claim 6 wherein:
   the surrounding region extends beyond the core region at the distal end.

8. A catheter as in claim 1 wherein the guidewire tapers from a smaller diameter at the distal end to a larger diameter away from the distal end.

9. A catheter comprising:
   a guidewire extending from a proximal end to a distal end,
   the guidewire including a first region of its length near the distal end wherein the cross-section of the guidewire in the first region is smaller than the cross-section of the guidewire at locations proximal to the first region,
   the guidewire also including a tapered region at its distal end tapering in a direction toward said distal end;
   an inflatable dilatation balloon wrapped around the guidwire in the first region and releasably bonded to itself to remain wrapped until inflated; and
   inflation means communicating with the balloon for breaking the releasable bond and inflating the balloon.

10. A catheter comprising:
    a dilatation balloon adapted to be inflated to thereby change from a collapsed state to an inflated state;
    a tubular member coupled to the balloon for communicating with the balloon to enable inflation thereof; and
    means for releasably bonding the dilatation balloon in its collapsed state to itself to thereby secure the balloon in its collapsed state until the balloon is inflated.

11. A catheter as in claim 10 wherein the means for releasably bonding comprises a glue.

12. A catheter as in claim 10 wherein the means for releasably bonding comprises ultrasonic bonding of the balloon to itself.

13. A catheter as in claim 10 wherein the balloon is wrapped in a spiral configuration before being bonded.

* * * * *